United States Patent [19]

Hodgen

[11] Patent Number: 5,516,769
[45] Date of Patent: May 14, 1996

[54] METHOD OF INHIBITING FERTILIZATION

[75] Inventor: Gary D. Hodgen, Norfolk, Va.

[73] Assignee: The Medical College of Hampton Roads, Norfolk, Va.

[21] Appl. No.: 19,791

[22] Filed: Feb. 19, 1993

[51] Int. Cl.$^6$ .................................................. A61K 31/56
[52] U.S. Cl. ............................................. 514/179; 514/843
[58] Field of Search ................................... 514/179, 843

[56] References Cited

U.S. PATENT DOCUMENTS

| | | | |
|---|---|---|---|
| 3,890,356 | 6/1975 | Grunwell et al. | 260/397.5 |
| 3,928,398 | 12/1975 | Grunwell et al. | 260/397.5 |
| 4,000,273 | 12/1976 | Grunwell et al. | 424/238 |
| 4,416,822 | 11/1983 | Campbell | 260/397.4 |
| 4,670,426 | 6/1987 | Zor et al. | 514/171 |
| 5,262,408 | 11/1993 | Bergink | 514/182 |

FOREIGN PATENT DOCUMENTS 145493  6/1985  European Pat. Off. .

OTHER PUBLICATIONS

Batista et al., Delayed Endometrical Maturation Induced by Daily Administration of the Antiprogestin RU 486: A Potential New Contraceptive Strategy, Am J Obstet Gynecol, 167:60, 1992.
Sheth et al., A Randomized, Double–Blind Study of Two Combined and Two Progestogen–Only Oral Contraceptives, Contraception, 25:243, 1982.
Collins et al., Blockade of the spontaneous midcycle gonadotropin surge in monkeys by RU 486, J Clin Endocrinol Metab, 63:1270, 1986.
Danforth et al., Contraceptive Potential of RU 486 By Ovulation Inhibition III Preliminary Observations on Once Weekly Oral Administration, Contraception, 40:195, 1989.
Shoupe et al., Effects of an antiprogenterone RU 486 in normal women II: administration in the late follicular phase, Am J Obstet Gynecol, 157:1421, 1987.
Liu et al., Disruption of follicular maturation and delay of ovulation after administration of the antiprogesterone Ru 486, J Clin Endocrinol Metab. 65:1135, 1987.
Luukkainen et al., Inhibition of folliculogenesis and ovulation by the antigesterone RU 486, Fert Steril, 49:961, 1988.
Messinis et al., The Effect of the Antiprogestin Mifepristone RU–486 On Maturion and In–Vitro Fertilization of Human Oocytes, Br J Obstet Gynecol, 95(6), 1988–Abstract.
Juneja et al., In Vitro Effect of RU 486 On Sperm–Egg Interaction in Mice, Am J Obstet Gynecol, 163:216, 1990.
Chwalisz et al., Inhibition of Estradiol–Mediated Endometrial Gland Formation by the Antigestagen Onapirstone In Rabbits: Relationship to Uterine Estrogen Receptors, Endocrinology 129:312, 1991—Abstract.
Anon., Research Diclosure 28976, 1988.
Hodgen, Surrogate Embryo Transfer Combined with Estrogen–Progesterone Therapy in Monkeys, JAMA 250:2167, 1983.
Chillik et al., Characterizing Pituitary Response to Gonadotropin–releasing Hormone (GnRH) Antagonist in Monkeys: Tonic Follicle–stimualating Hormone/luteinizing Hormone Secretion Versus Acute GnRH Challenge Tests Before, During and After Treatment, Fert. Steril. 48:480, 1987.
Yoshimura et al., Progesterone Protected Oocytes from Premature Degeneration within the Follicle, Nippon Sanka Fujinka Gakkai Zasshi, 42(9):1256, 1990—Abstract.
Sakiz et al. R 2323—An Original Contraceptive Compound, Excerpta Medica, Abs. 86, 1970.
Spitz, Clinical Applications of the Antiprogestin RU 486, The Endocrinologist, 3:58, 1993.

*Primary Examiner*—Kimberly Jordan
*Attorney, Agent, or Firm*—Ostrolenk, Faber, Gerb & Soffen

[57] ABSTRACT

Fertilization of an oocyte is inhibited by administering a fertilizing inhibitory amount of an antiprogestin to an ovulatory mammal in an amount which is insufficient to prevent ovulation but sufficient to inhibit fertilization, while the regularity of the menstrual cycle is sustained.

19 Claims, 1 Drawing Sheet

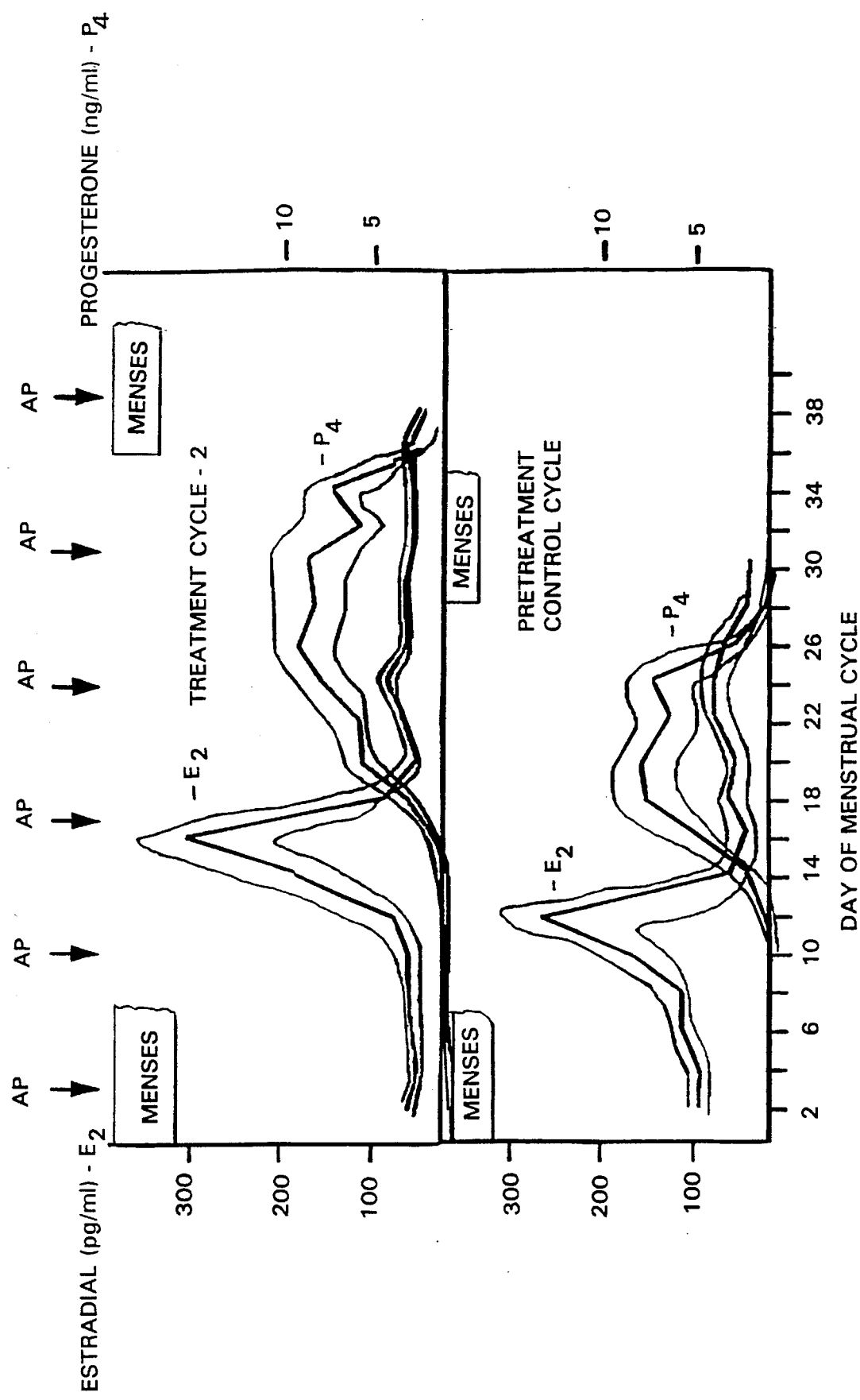

METHOD OF INHIBITING FERTILIZATION

BACKGROUND OF THE INVENTION

The ovarian/menstrual cycle is a complex event characterized by two distinct phases, namely the estrogen rich follicular phase and, after ovulation, the progesterone rich luteal phase. Each has a duration of approximately 14 days resulting in an intermenstrual interval of about 28 days. The endometrial tissue responds to the changes in hormonal milieu.

The onset of menstruation is the begining of a new menstrual cycle and is counted as day 1. During a span of about 5 to 7 days, the superficial layers of the endometrium, which grew and developed during the antecedent ovarian/menstrual cycle, are sloughed because demise of the corpus luteum in the non-fertile menstrual cycle is associated with a loss of progesterone secretion. Ovarian follicular maturation occurs progressively resulting in a rise in the circulating levels of estrogen, which in turn leads to new endometrial proliferation (i.e. mitogenesis induced by the estrogen), predominantly during the second week of follicular maturation.

The dominant ovarian follicle undergoes ovulation at mid-cycle, generally between menstrual cycle days 12 to 16. The follicle is converted from a predominantly estrogen source to a predominantly progesterone source (the corpus luteum).

Ovulation occurs when the oocyte is potentially competent to achieve fertilization, subsequent development and implantation as an embryo. The increasing level of progesterone in the blood converts the proliferative endometrium to a secretory phase in which the tissue proliferation has promptly abated, leading to the formation of endometrial glands or organs. When the ovulated oocyte is viably fertilized and continues its progressive embryonic cleavage, the secretory endometrium and the conceptus can interact to bring about implantation (nidation), beginning about 6 to 8 days after fertilization.

If an ongoing pregnancy is to be established via implantation, the embryo will attach and burrow into the secretory endometrium and begin to produce human chorionic gonadotropin (hCG). The hCG in turn stimulates extended corpus luteum function, i.e. the progesterone production remains elevated, and menses does not occur in the fertile menstrual cycle. Pregnancy is then established.

Pregnancy may not occur for a variety of reasons including, inter alia, absence of competent sperm, lack of fertilization despite exposure of the oocyte to sperm, lack of a competent embryo to achieve implantation, lack of competant endometrium to support implantation, and ineffective subsequent events of placentation and fetal development.

In the non-fertile menstrual cycle, the waning level of progesterone in the blood causes the endometrial tissue to be sloughed. This starts a subsequent menstrual cycle.

Because endometrial proliferation serves to prepare the uterus for an impending pregnancy, manipulation of hormones and of the uterine environment can provide contraception. For example, estrogens are known to decrease follicle stimulating hormone secretion by feedback inhibition. Under certain circumstances, estrogens can also inhibit luteinizing hormone secretion, once again by negative feedback. Under normal circumstances, the spike of circulating estrogen found just prior to ovulation induces the surge of gonadotropic hormones that occurs just prior to and resulting in ovulation. High doses of estrogen immediately post-coitally also can prevent conception probably due to interference with implantation.

Progestins can also provide contraception. Endogenous progesterone after estrogen is responsible for the progestational changes of the endometrium and the cyclic changes of cells and tissue in the cervix and the vagina. Administration of progestin makes the cervical mucus thick, tenacious and cellular which is believed to impede spermatozoal transport. Administration of progestin also inhibits luteinizing hormone secretion and blocks ovulation in humans.

The most prevalent form of oral contraception is a pill that combines both an estrogen and a progestin, a so-called combined oral contraceptive preparation. Apparently, the progestin acts to block gonadotropin release; the estrogen component provides endometrial control to diminish breakthrough bleeding.

Alternatively, there are contraceptive preparations that comprise progestin only. However, the progestin-only preparations have a more varied spectrum of side effects than do the combined preparations, especially more breakthrough bleeding. As a result, the combined preparations are the preferred oral contraceptives in use today (Sheth et al., *Contraception* 25:243, 1982).

Antiprogestins (sometimes termed "progesterone antagonists" or "anti-gestagens") are a class of materials that block the progesterone receptor. For example, mifepristone (RU 486) is a progesterone receptor antagonist. RU 486 binds to the progesterone receptor and produces a blockade of the binding of progesterone to its receptor. When administered in the luteal phase of the menstrual cycle, RU 486 induces vaginal bleeding.

Unlike the invention described herein, the prior art has demonstrated either inhibition of the ovulatory menstrual cycle or delayed endometrial maturation. It has been demonstrated in primate models that both a single injection of the antiprogestin RU 486 (5 mg/kg, IM) in the late follicular phase or a once weekly oral RU 486 dose of 25 mg prevented ovulation (Collins et al., *J. Clin. Endocrinol. Metab.* 1986, 63:1270–1276; Danforth et al., *Contraception* 1989, 40:195–200).

Using various study protocols which differed in regimen and dose, it has been demonstrated by several groups of investigators that RU 486 inhibits ovulation in women as well (Shoupe et al., *Am. J. Obstet. Gynecol.* 1987, 157:1421–1426; Liu et al., *J. Clin. Endocrinol. Metab.* 1987, 65:1135–1140; Luukkainen et al., *Fertil. Steril.* 1988, 49:961–963).

That RU 486 in low dose administration may exhibit an anti-implantation effect in women has been postulated (Spitz et al., *The Endocrinology* 1993, 3:1, 58 et seq.). Others have demonstrated an influence of RU 486 on endometrial histology, including delayed endometrial maturation (Batista et al., *Am. J. Obstet. Gynecol.* 1992, 167:60–65). The invention described herein, which is distinct from the prior art, is based on the inhibition of gamete maturation and the fertilization process. Prior art has not demonstrated any such contraceptive effect.

The inventor has discovered that a sufficiently low dose administration of an antiprogestin functions as a contraceptive, but not based on an anti-nidatory effect. Rather, maturation and/or fertilization of the oocyte is prevented and/or inhibited, unrelated to whether implantation could occur.

It is, accordingly, the object of this invention to provide a new method of preventing or inhibiting normal oocyte fertilization without inhibiting ovulation of a mammal, especially primates. This and other objects of the invention will become apparent to those of ordinary skill in this art from the following description.

BRIEF DESCRIPTION OF THE DRAWING

The sole FIGURE shows the patterns of serum estradiol and progesterone realized in Example 1 below.

SUMMARY OF THE INVENTION

This invention broadly relates to a method of preventing or inhibiting normal fertilization. More particularly, it relates to a method of inhibiting normal fertilization of an oocyte by administering an amount of an antiprogestin to an ovulatory mammal sufficient to inhibit fertilization, said administration regimen being not enough to prevent ovulation and being insufficient to interfere with the regularity of the mammal's ovulatory menstrual cycle.

DESCRIPTION OF THE INVENTION

In accordance with the present invention, a quantity of an antiprogestin which is insufficient to interfere with the regularity of the individual ovulatory menstrual cycle of a mammal is administered to that mammal. Some minor changes in the cycle may be observed, for instance the cycle length may increase and endometrial maturation may, or may not, be delayed. As used herein, the term "regularity" means the maintaince of spontaneous menustration at periodic intervals. When the amount of the antiprogestin is sufficiently large, ovulation is prevented and such an amount is not used in the present invention. As a result of the sufficiently low dose administration regimen of the antiprogestin, maturation and/or fertilization of the oocyte is prevented or inhibited in the present invention. This amount is hereinafter referred to as a "fertilizing inhibitory amount".

The antiprogestin can be a progesterone receptor antagonist or any pharmaceutically suitable agent that counteracts the normal biological activity of progesterone. A preferred antiprogestin is a progesterone receptor antagonist. For example, RU 486 is particularly suitable in the practice of this invention.

Examples of antiprogestins which can be employed in this invention are RU 486 ("mifepristone", Roussel Uclaf, Paris; U.S. Pat. No. 4,386,085); and "onapristone" (Schering Ag, Berlin; U.S. Pat. No. 4,780,461) and the steroids described in the following patents and patent applications: U.S. Pat. No. 4,609,651, especially the compound lilopristone (11β-(4-dimethylaminophenyl)- 17β-hydroxy-17α-(3-hydroxyprop-1-(Z)-enzyl- 4,9(10) estradien-3-one); U.S. application Ser. No. 06/827,050, especially the compounds 11β-(4-acetylphenyl)- 17β-hydroxy-17α-(1-propinyl)-4,9-estradien- 3-one and 11β-(4-acetylphenyl)-17β-hydroxy-17α-(3-hydroxy- 1(2)-propenyl)-4,9-estradien-3-one; U.S. application Ser. No. 07/283,632; published European patent application EP-A 04042831; and other anti-gestations, e.g., U.S. Pat. No. 4,891,368.

The antiprogestin can be administered by way of any art recognized means as practiced in the pharmaceutical arts. For example, a suitable antiprogestin may be so formulated so that it can be administered orally, via a skin patch for transdermal absorption, contained within an inert matrix which is implanted within the body and in the depot state or intravaginally in a matrix that slowly releases the antiprogestin (such implants are taught in U.S. Pat. Nos. 4,957, 119 and 5,088,505 and the like).

Pharmaceutical formulations containing the antiprogestin and a suitable carrier can be solid dosage forms which includes tablets, capsules, cachets, pellets, pills, powders or granules; topical dosage forms which includes solutions, powders, fluid emulsions, fluid suspensions, semi-solids, ointments, pastes, creams, gels or jellies and foams; and parenteral dosage forms which includes solutions, suspensions, emulsions or dry powder comprising an effective amount of antiprogestin as taught in this invention. It is known in the art that the active ingredient, the antiprogestin, can be contained in such formulations in addition to pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modern Pharmaceutics", Banker & Rhodes, Marcel Dekker, Inc. 1979; "Goodman & Gilman's The Pharmaceutical Basis of Therapeutics", 6th Edition, MacMillan Publishing Co., New York 1980 can be consulted.

The pharmaceutical formulations may be provided in kit form containing at least about 20, and preferably about 28 tablets, intended for ingestion on successive days of the menstrual cycle. Where administration of the antiprogestin is intended to be periodic, a plurality, generally at least three, of non-adjacent tablets contain the antiprogestin while the remaining tablets are placebo. Where administration is intended to be daily, generally at least about 20 of the tablets contain the antiprogestin.

The inhibitory effective amount of an antiprogestin in the practice of this invention can be determined using art-recognized methods, for example, by establishing dose-response curves in suitable primate models and extrapolating to humans, extrapolating from suitable in vitro systems or by determining effectiveness in clinical trials. The dosage range will be between the least amount necessary to inhibit fertilization and the greatest amount which will not prevent ovulation or otherwise interfere with the regularity of the mammal's menstrual cycle. The determination of an effective dose is a routine exercise in the pharmaceutical arts. The artisan will take into account various physical parameters of the prospective host such as weight, age and the like.

In like vein, the dosage regimen of the preparation is determinable using art-recognized methods such as establishing a dose response curve in similar primate models or in a suitable in vitro experimental system or by an empirical determination in clinical trials.

The administration of the antiprogestin can either be periodic such as on a weekly basis or continuous, that is on a daily basis. A continuous daily administration is preferred not because of demonstrated efficiency of action but rather for compliancy; individuals are more likely to follow the treatment regimen and not to forget or overlook a periodic administration schedule. In the case of the antiprogestin RU 486, a suitable human oral dose will be on the order of about 0.01 to 1 mg per dose daily, preferably about 0.05 to 0.5 mg per dose daily. This amount can be lowered or raised based on the administration regimen and based on the characteristics of the individual receiving the treatment. With other antiprogestins, different milligram dose amounts may be appropriate depending on potency, mode of administration and the like factors. Variations of dosage based on the route of administration may vary and such changes can be determined practicing known techniques.

Without being limited to theory, practice of the present invention inhibits maturation and/or fertilization of the oocyte. This may be the result of incomplete or inadequate activation of the oocyte, inadequate association of the oocyte with competent sperm, inadequate embryo cleavage, inadequate gamete interaction, alteration of gamete transport or failure of implantation due to incompetence of the oocyte or the embryo thereof, or a combination of one or more of the foregoing. Whatever the mechanism involved, normal fertilization (i.e. where the oocyte undergoes progressive embryonic cleavage sufficient to successfully complete implantation and continued embryonic cleavage thereafter) does not occur. Additionally, while a characteristic of the active agent of this invention is that it is progesterone receptor antagonist (an antiprogestin), a different common characteristic of these agents may be responsible for the fertilizion inhibitory effect.

In order to further illustrate the present invention, specific examples are set forth below. It will be appreciated, however, that these examples are illustrative only and are not intended to limit the scope of the invention.

EXAMPLE 1

For the purposes of this study, the antiprogestin selected was RU 486 and this was administered in doses of 12.5 mg once weekly to female monkeys, which are recognized to be a suitable model for human research. The end points in this study were the serum levels of estradiol and progesterone, the timeliness and duration of menses, the presence or absence of pregnancy after timed coital exposures and the determination of whether the oocytes ovulated became fertilized during the drug treatment cycles.

The study was carried out at the Eastern Virginia Medical School which maintains a fully accredited animal research facility which complies through its animal care and use committee with the review standards set forth in the National Institute of Health's "Guide for Care and Use of Laboratory Animals", the Public Health Services' "Principles for the Care and Use of Laboratory Animals", and the United States Department of Agriculture's Implementation Regulations of the 1985 Amendments for the Animal Welfare Act.

Tablets containing the antiprogestin were administered orally (by gavage) on the third, tenth, seventeenth and twenty-fourth day after the onset of menses. Menses and/or breakthrough bleeding were monitored by daily vaginal swabs.

In the first stage of the study, 9 normal adult female monkeys (*Macaca fascicularis*) and two proven breeder males were studied over the course of seven consecutive menstrual cycles. The initial cycle was the qualification for acceptance into the protocol based on apparent ovulation. This was followed by three consecutive cycles where treatment by the antiprogestin was conducted and followed by three post-treatment recovery cycles. All of the females were caged with a fertile male on cycle days 13 through 18 and mating was confirmed by the presence of semen plugs in the vagina. Femoral blood was collected on alternate days throughout the initial control cycle and treatment cycle two and was otherwise collected on cycle day 23 to measure progesterone (>2 ng/ml) as a marker of apparent ovulation.

The FIGURE shows the control patterns of serum estradiol and progesterone in the control cycle in the lower panel and in treatment cycle 2 in the upper panel. It will be seen that despite a slight temporal distortion of the cycle, i.e., a shift to the right in the follicular phase, these endocrine parameters suggest that ovulation did occur. The serum levels of ovarian steroids are in the normal range. However, the duration of menses was shorter when the females were receiving the once weekly antiprogestin as compared to the control cycles, 1.7+0.9 as opposed to 4.9+1.0 days (p< 0.05), respectively. Breakthrough bleeding remained incidental in all cycles and was not a differential factor.

Table I below summarizes pertinent observations:

TABLE 1

RESPONSE OF THE OVARIAN/MENSTRUAL CYCLE TO WEEKLY
LOW DOSE ANTI-PROGESTIN WITH EXPOSURE FOR CONCEPTION

Days (X + SEM)

| Cycle Group | N | Menses | Follicular Phase | Apparent Ovulation | Luteal Phase | Cycle Length | Cumulative Pregnancies[1] |
|---|---|---|---|---|---|---|---|
| Control | 9 | 4.1 ± 1.0 | 13.6 ± 2.2 | 9/9 | 15.2 ± 2.1 | 28.3 ± 2.7 | — |
| Treatment Cycle - 1 | 9 | 2.0 ± 0.4 | 17.4 ± 4.0 | 9/9 | 14.9 ± 1.7 | 33.5 ± 4.1 | 0/9 |
| Treatment Cycle - 2 | 9 | 1.7 ± 0.9 | 18.7 ± 5.5 | 9/9 | 16.2 ± 2.5 | 35.7 ± 3.0 | 0/9 |
| Treatment Cycle - 3 | 9 | 1.9 ± 1.1 | 17.9 ± 4.4 | 7/9 | 15.0 ± 1.2 | 34.5 ± 4.9 | 0/9 |
| Recovery Cycle - 1 | 9 | 2.1 ± 0.7 | 15.0 ± 2.8 | 8/9 | 15.7 ± 2.7 | 30.1 ± 4.2 | 2/9 |
| Recovery Cycle - 2 | 9 | 3.7 ± 1.2 | 13.2 ± 3.1 | 6/7 | 14.8 ± 3.3 | 28.1 ± 3.3 | 5/9 |
| Recovery Cycle - 3 | 8 | 3.6 ± 0.8 | 14.1 ± 2.6 | 2/3[2] | 15.1 ± 3.0 | 29.4 ± 4.4 | 7/8[3] |

[1]Pregnancies were detected by mCG via urinary test kits.
[2]One monkey was eliminated from the study due to injury from the male.
[3]Six of 7 pregnancies resulted in normal term deliveries.

Table 1 shows reduced duration of menses (p<0.05), longer follicular phases (p<0.05), and no change in luteal phase length (p>0.05) were evident during the intermittent low dose antiprogestin regiment period. Of particular significance are three observations. First the ovarian/menstrual cycles continued in an almost "normal" fashion. Second, the once weekly antiprogestin regimen reliably prevented contraception. Third, there was a rapid recovery ("reversibility") from fertility control, with some pregnancies beginning in the initial post-treatment cycle and others in the second and third cycles after the treatment had ended.

A second phase of the study was conducted in order to elucidate the primary contraceptive mechanism of action of the antiprogestin. In this phase, 14 female monkeys were subjected to the same treatment and coital protocol for one cycle as described above except that on menstrual cycle day 23, laparotomy was done in order to allow retrograde lavage of the reproductive track potentially in order to collect oocytes and/or pre-embryos. Additionally, an endometrial wedge was taken from each monkey on that day and evaluated histologically in order to access appropriateness of secretory tissue maturation. Table 2 summarizes the results.

TABLE 2

| Total Oocytes Collected | Cleaved and/or Fertilized Oocytes | "Normal" Oocytes (intact) | Degenerate Oocytes (dark Cytoplasm) | Subsequent Pregnancies[1] |
|---|---|---|---|---|
| 11 | 0 | 7 | 4 | 0 |

[1] One monkey had an anovulatory menstrual cycle.

The endometrial thickness was noted to be markedly reduced (about 60%) compared to temporally controls in mid-luteal phase. The endometrium of 12 of the 14 monkeys was at a very early secretory phase when biopsies were taken on day 23, that is they were not synchronous with the observed serum profiles of estradiol and progesterone even though onset of the luteal phase was delayed until cycle day 17 or 18 by the RU 486 therapy.

Eleven unfertilized oocytes were recovered of which four were degenerate. No cleaving pre-embryos were noted and no pregnancies subsequently occurred. It is noteworthy that the oocytes did not have zona bound sperm attached to them. Thirteen of the 14 monkeys had apparently ovulatory/menstrual cycles during the once weekly oral doses of 12.5 mg of RU 486, as assessed by the presence of an identifiable corpus luteum at laparotomy on cycle day 23.

The findings in the above studies demonstrate that when using a low dose administration regimen of anti-progestin therapy, ovulatory/menstrual cycles can be maintained while simultaneously achieving a contraceptive action through the primary mechanism of inhibiting normal oocyte fertilization. Even though the follicular phases of the antiprogestin treatment cycles were slightly extended, the regularity of menses was not deterred. The duration of the menses was reduced. The cumulative conception rate in post-treatment cycles is comparable to never treated females which indicates a rapid and full reversibility.

EXAMPLES 2–5

The study described in Example 1 is repeated except that the following antiprogestins are substituted for RU 486:

| Example | Antiprogestin |
|---|---|
| 2 | onapristone |
| 3 | lilopristone |
| 4 | 11β-(4-acetylphenyl)-17β-hydroxy-17α-(1-propinyl)-4,9-estradien-3-one |
| 5 | 11β-(4-acetylphenyl)-17β- |

-continued

| Example | Antiprogestin |
|---|---|
| | hydroxy-17α-(3-hydroxy-1(2)-propenyl)-4,9-estradien-3-one |

It will be appreciated that a reliable contraceptive method which can sustain endogenous ovarian steroid secretion within the physiologic zone is an attractive alternative to existing exogenous hormonal formulations that prevent ovulation and artificially regulate menses. This can be achieved, as demonstrated by the foregoing results which used RU 486 as a model antiprogestin in a once weekly low dose regiment. It should be observed that the study described above in Example 1 did not attempt to determine the lowest effective dose of the antiprogestin.

Application of the compounds, compositions and methods of the present invention for the medical or pharmaceutical uses described can be accomplished by any clinical, medical, and pharmaceutical methods and techniques as are presently or prospectively known to those skilled in the art. It will therefore be appreciated that the various embodiments which have been described above are intended to illustrate the invention and various changes and modifications can be made in the inventive method without departing from the spirit and scope thereof.

What is claimed is:

1. A method of inhibiting fertilization of an oocyte which comprises administering a fertilizing inhibitory amount of an antiprogestin to an ovulatory mammal, said amount being insufficient either to prevent ovulation or to interfere with the regularity of the ovarian menstrual cycle of the mammal.

2. The method of claim 1, in which the antiprogestin is administered a plurality of times periodically during the menstrual cycle.

3. The method of claim 1, in which the antiprogestin is administered daily for at least about 20 days of the menstrual cycle.

4. The method of claim 3, in which the administration is oral.

5. The method of claim 1, in which the administration is oral.

6. The method of claim 1, in which the mode of administration is by depot.

7. The method of claim 1, in which the amount administered to the mammal contains about 0.01 to 1 mg of the antiprogestin.

8. The method of claim 7, in which the amount is about 0.05 to 0.5 mg.

9. The method of claim 1, in which the mammal is human.

10. The method of claim 1, in which the antiprotestin is a progesterone receptor antagonist.

11. The method of claim 9, in which the antiprogestin is RU 486.

12. The method of claim 1 in which exogenous progestin is not administered to the mammal.

13. A kit containing at least about 20 tablets which are intended to be taken on successive days, wherein at least three of the tablets which are not adjacent to each other contain a fertilization inhibitory amount of an antiprogestin, said amount being insufficient either to prevent ovulation or to interfere with the regularity of the ovarian menstrual cycle of a mammal.

14. The kit of claim 13, in which each of said about 20 tablets contains said fertilization inhibitory amount of an antiprogestin.

15. The kit of claim 13, in which said amount is about 0.01 to 1 mg.

16. The kit of claim 15, in which said amount is about 0.05 to 0.5 mg.

17. The kit of claim 16 in which said antiprogestin is RU 486.

18. The kit of claim 13 containing about 28 tablets, at least about 20 of such tablets containing a fertilization inhibitory amount of an antiprogestin.

19. A method of inhibiting fertilization of an intact oocyte which comprises administering a fertilizing inhibitory amount of an antiprogestin to an ovulatory mammal, said amount being insufficient to either prevent ovulation or to interfere with the regularity of the ovarian intermenstrual interval of the mammal.

* * * * *